(12) United States Patent
Cohen et al.

(10) Patent No.: US 9,498,214 B2
(45) Date of Patent: Nov. 22, 2016

(54) SURGICAL STAPLING APPARATUS WITH CLAMPING ASSEMBLY

(71) Applicant: Covidien LP, Mansfield, MA (US)

(72) Inventors: Matthew D. Cohen, Berlin, CT (US); Jennifer Broom, Branford, CT (US); (Continued)

(73) Assignee: Covidien LP, Mansfield, MA (US)

( * ) Notice: Subject to any disclaimer, the term of this patent is extended or adjusted under 35 U.S.C. 154(b) by 492 days.

(21) Appl. No.: 14/047,275

(22) Filed: Oct. 7, 2013

(65) Prior Publication Data

US 2014/0034703 A1 Feb. 6, 2014

Related U.S. Application Data

(63) Continuation of application No. 13/465,102, filed on May 7, 2012, now Pat. No. 8,550,325, which is a (Continued)

(51) Int. Cl.
*A61B 17/068* (2006.01)
*A61B 17/072* (2006.01)
(Continued)

(52) U.S. Cl.
CPC ....... *A61B 17/068* (2013.01); *A61B 17/07207* (2013.01); *A61B 17/28* (2013.01); (Continued)

(58) Field of Classification Search
USPC ................................................ 227/19, 175.1
See application file for complete search history.

(56) References Cited

U.S. PATENT DOCUMENTS 3,837,555 A 9/1974 Green
4,120,302 A 10/1978 Ziegler
(Continued)

FOREIGN PATENT DOCUMENTS

EP 1785098 A2 5/2007
EP 1 550 411 B1 7/2009
(Continued)

OTHER PUBLICATIONS

European Search Report for Application No. 09251420.7 dated Sep. 7, 2009. (2 pages).
(Continued)

*Primary Examiner* — Brian D Nash (57) ABSTRACT

A surgical stapling apparatus includes a handle assembly and an elongate portion extending distally from the handle assembly. An end effector disposed adjacent a distal portion of the elongate portion includes an anvil assembly and a cartridge assembly, wherein at least one of the cartridge assembly and the anvil assembly is movable with respect to the other to move the end effector between an open configuration where the cartridge assembly and the anvil assembly are substantially spaced and a closed configuration where the cartridge assembly and the anvil assembly are closer together. The end effector also includes a clamping assembly including a first clamping surface deployable to extend laterally from the anvil assembly, and a second clamping surface deployable to extend laterally from the cartridge assembly such that, when deployed, the first and second clamping surfaces oppose one another when the cartridge assembly is in the closed position.

15 Claims, 10 Drawing Sheets

(72) Inventors: Christina Rideout, Middletown, CT (US)

Related U.S. Application Data continuation of application No. 13/273,641, filed on Oct. 14, 2011, now Pat. No. 8,186,557, which is a continuation of application No. 12/414,918, filed on Mar. 31, 2009, now Pat. No. 8,113,409.

(51) Int. Cl.

| *A61B 17/28* | (2006.01) |
|---|---|
| *A61B 18/08* | (2006.01) |
| *A61B 18/14* | (2006.01) |
| *A61B 17/00* | (2006.01) |
| *A61B 17/29* | (2006.01) |
| *A61B 17/32* | (2006.01) |

(52) U.S. Cl.
CPC .......... *A61B 18/085* (2013.01); *A61B 18/1445* (2013.01); *A61B 2017/00557* (2013.01); *A61B 2017/00893* (2013.01); *A61B 2017/07264* (2013.01); *A61B 2017/2926* (2013.01); *A61B 2017/2927* (2013.01); *A61B 2017/320052* (2013.01)

(56) References Cited

U.S. PATENT DOCUMENTS

| 4,349,028 | A | 9/1982 | Green |
|---|---|---|---|
| 4,488,523 | A | 12/1984 | Shichman |
| 4,505,414 | A | 3/1985 | Filipi |
| 4,607,620 | A | 8/1986 | Storz |
| 4,610,252 | A | 9/1986 | Catalano |
| 4,681,109 | A | 7/1987 | Arroyo |
| 4,803,983 | A | 2/1989 | Siegel |
| 4,848,367 | A | 7/1989 | Avant et al. |
| 4,873,977 | A | 10/1989 | Avant et al. |
| 4,881,545 | A | 11/1989 | Isaacs et al. |
| 5,018,657 | A | 5/1991 | Pedlick et al. |
| 5,047,039 | A | 9/1991 | Avant et al. |
| 5,059,198 | A | 10/1991 | Gimpelson |
| 5,219,111 | A | 6/1993 | Bilotti et al. |
| 5,336,228 | A | 8/1994 | Cholhan |
| 5,354,312 | A | 10/1994 | Brinkerhoff et al. |
| 5,474,057 | A | 12/1995 | Makower et al. |
| 5,591,173 | A | 1/1997 | Schifano |
| 5,626,607 | A | 5/1997 | Malecki et al. |
| 5,676,674 | A | 10/1997 | Bolanos et al. |
| 5,681,349 | A | 10/1997 | Sugarbaker |
| 5,702,409 | A | 12/1997 | Rayburn et al. |
| 5,752,965 | A | 5/1998 | Francis et al. |
| 5,769,892 | A | 6/1998 | Kingwell |
| 5,853,412 | A | 12/1998 | Mayenberger |
| 5,855,590 | A | 1/1999 | Malecki et al. |
| 5,865,361 | A | 2/1999 | Milliman et al. |
| 5,891,162 | A | 4/1999 | Sugarbaker et al. |
| 5,904,702 | A | 5/1999 | Ek et al. |
| 5,921,996 | A | 7/1999 | Sherman |
| 5,928,253 | A | 7/1999 | Sherman et al. |
| 5,928,264 | A | 7/1999 | Sugarbaker et al. |
| 5,997,567 | A | 12/1999 | Cangelosi |
| 6,013,095 | A | 1/2000 | Ouchi |
| 6,036,706 | A | 3/2000 | Morejohn et al. |
| 6,053,933 | A | 4/2000 | Balazs et al. |
| 6,146,394 | A | 11/2000 | Morejohn et al. |
| 6,205,699 | B1 | 3/2001 | Bogni |
| 6,293,954 | B1 | 9/2001 | Fogarty et al. |
| 6,468,285 | B1 | 10/2002 | Hsu et al. |
| 6,626,922 | B1 | 9/2003 | Hart et al. |
| 6,887,240 | B1 | 5/2005 | Lands et al. |
| 6,939,353 | B2 | 9/2005 | Que et al. |
| 6,942,675 | B1 | 9/2005 | Vargas |
| 7,001,408 | B2 | 2/2006 | Knodel et al. |
| 7,041,113 | B2 | 5/2006 | Gruhl et al. |
| 7,118,528 | B1 | 10/2006 | Piskun |
| 7,144,409 | B2 | 12/2006 | Aranyi |
| 7,204,836 | B2 | 4/2007 | Wagner et al. |
| 7,354,444 | B2 | 4/2008 | Burbank et al. |
| 7,451,904 | B2 | 11/2008 | Shelton, IV |
| 7,470,276 | B2 | 12/2008 | Tu |
| 7,481,347 | B2 | 1/2009 | Roy |
| 7,559,937 | B2 | 7/2009 | de la Torre et al. |
| 7,673,780 | B2 | 3/2010 | Shelton et al. |
| 7,799,039 | B2 | 9/2010 | Shelton et al. |
| 7,828,186 | B2 | 11/2010 | Wales |
| 7,861,907 | B2 | 1/2011 | Green et al. |
| 2003/0236537 | A1 | 12/2003 | Hart et al. |
| 2004/0176779 | A1 | 9/2004 | Casutt et al. |
| 2004/0243177 | A1 | 12/2004 | Svehla et al. |
| 2005/0145671 | A1 | 7/2005 | Viola |
| 2005/0184121 | A1 | 8/2005 | Heinrich |
| 2005/0192605 | A1 | 9/2005 | Hart et al. |
| 2005/0230453 | A1 | 10/2005 | Viola |
| 2005/0274768 | A1 | 12/2005 | Cummins et al. |
| 2006/0025813 | A1 | 2/2006 | Shelton et al. |
| 2006/0085031 | A1* | 4/2006 | Bettuchi .......... A61B 17/00491 606/215 |
| 2006/0085033 | A1 | 4/2006 | Criscuolo et al. |
| 2006/0111738 | A1 | 5/2006 | Wenchell |
| 2006/0163312 | A1 | 7/2006 | Viola et al. |
| 2006/0180634 | A1 | 8/2006 | Shelton, IV et al. |
| 2006/0190028 | A1 | 8/2006 | Wales et al. |
| 2007/0021761 | A1 | 1/2007 | Phillips |
| 2007/0034668 | A1 | 2/2007 | Holsten et al. |
| 2007/0073340 | A1* | 3/2007 | Shelton, IV ..... A61B 17/07207 606/219 |
| 2007/0095877 | A1 | 5/2007 | Racenet et al. |
| 2007/0102453 | A1 | 5/2007 | Morgan et al. |
| 2007/0106295 | A1 | 5/2007 | Garrison et al. |
| 2007/0125826 | A1* | 6/2007 | Shelton, IV ..... A61B 17/07207 227/175.1 |
| 2007/0175954 | A1 | 8/2007 | Viola |
| 2007/0187456 | A1 | 8/2007 | Viola et al. |
| 2008/0078800 | A1 | 4/2008 | Hess et al. |
| 2008/0078807 | A1* | 4/2008 | Hess .................. A61B 17/0644 227/181.1 |
| 2008/0078808 | A1 | 4/2008 | Hess et al. |
| 2008/0082124 | A1 | 4/2008 | Hess et al. |
| 2008/0283570 | A1* | 11/2008 | Boyden ................ A61B 17/068 227/175.1 |
| 2008/0283572 | A1* | 11/2008 | Boyden ................ A61B 17/068 227/175.1 |
| 2008/0283577 | A1 | 11/2008 | Boyden et al. |
| 2009/0206123 | A1* | 8/2009 | Doll ................. A61B 17/07207 227/175.1 |
| 2009/0281554 | A1 | 11/2009 | Viola |
| 2009/0299340 | A1 | 12/2009 | Kazala et al. |
| 2010/0179382 | A1 | 7/2010 | Shelton et al. |
| 2010/0181364 | A1 | 7/2010 | Shelton et al. |
| 2012/0241491 | A1* | 9/2012 | Aldridge .......... A61B 17/07292 227/175.1 |
| 2012/0241505 | A1* | 9/2012 | Alexander, III . A61B 17/00491 227/179.1 |
| 2013/0075447 | A1* | 3/2013 | Weisenburgh, II ..................... A61B 17/00491 227/176.1 |
| 2013/0153641 | A1* | 6/2013 | Shelton, IV ......... A61B 17/068 227/180.1 |

FOREIGN PATENT DOCUMENTS

| GB | 2029754 | 3/1980 |
|---|---|---|
| WO | WO 02/17799 A1 | 3/2002 |
| WO | WO02/30296 | 4/2002 |
| WO | WO2006/055385 | 5/2006 |

OTHER PUBLICATIONS

European Search Report for Application No. 09251240 dated Oct. 5, 2009. (8 pages).

(56) References Cited

OTHER PUBLICATIONS

European Search Report for EP 10250635.9 date of completion is Jul. 14, 2010 (3 pages).

* cited by examiner

SURGICAL STAPLING APPARATUS WITH CLAMPING ASSEMBLY

CROSS-REFERENCE TO RELATED APPLICATIONS

This application is a continuation of U.S. patent application Ser. No. 13/465,102, now U.S. Pat. No. 8,550,325, filed May 7, 2012, which is a continuation of U.S. patent application Ser. No. 13/273,641, now U.S. Pat. No. 8,186,557, filed Oct. 14, 2011, which is a continuation of U.S. patent application Ser. No. 12/414,918, now U.S. Pat. No. 8,113,409, filed Mar. 31, 2009, the disclosures of each of the above-identified applications are hereby incorporated by reference in their entirety.

BACKGROUND

1. Technical Field

This application relates to a surgical stapling apparatus. More particularly, this application relates to a surgical stapling apparatus that includes structure for clamping tissue.

2. Related Art

Surgical stapling or fastener-applying devices for joining tissue are well known. Typically, such devices include an opposing jaw structure for grasping and clamping selected tissue, wherein one of the jaws of the opposing jaw structure includes a cartridge housing a plurality of staples or fasteners and the other jaw includes an anvil for formation of the fasteners.

Certain surgical stapling devices, for example, include two elongate jaw members for forming staples in generally linear rows. A cartridge containing staples arranged in two or more linear rows forms a tissue engaging surface of one of the jaw members, and an anvil having correspondingly arranged staple forming pockets forms an opposing tissue engaging surface of the other jaw member. The jaw members may be approximated to clamp the targeted tissue between the two tissue engaging surfaces. Thereafter the staples may be ejected from the cartridge toward the staple forming pockets to form rows of staples in the targeted tissue.

While employing a surgical stapler or similar device, a surgeon may experience difficulty while clamping tissue that is relatively thick; unduly strenuous effort may be required. To mitigate this difficulty, a surgeon will often pre-compress relatively thick tissue with a clamp prior to introducing the stapler, or apply clamps to adjacent tissue in conjunction with the stapler. These procedures require extra steps and devices and can be time consuming and expensive especially during endoscopic procedures.

SUMMARY

The present disclosure relates to a surgical stapling apparatus including a handle assembly, an elongate portion extending distally from the handle assembly and an end effector disposed adjacent a distal portion of the elongate portion. The end effector includes an anvil assembly including a fastener forming surface thereon and a cartridge assembly including a fastener ejection surface thereon through which surgical fasteners may be ejected. At least one of the cartridge assembly and the anvil assembly is movable with respect to the other between an open position wherein the cartridge assembly is substantially spaced from the anvil assembly and a closed position where the cartridge assembly and the anvil assembly are closer together. The end effector also includes a clamping assembly including a first clamping surface deployable to extend laterally from the fastener forming surface of the anvil assembly, and a second clamping surface deployable to extend laterally from the fastener ejection surface of the cartridge assembly such that, when deployed, the first and second clamping surfaces oppose one another when the cartridge assembly is in the closed position.

A portion of the first clamping surface may be deployable to extend distally from the fastener forming surface of the anvil assembly. A portion of the second clamping surface may be deployable to extend distally from the fastener ejection surface of the cartridge assembly.

The clamping assembly of the surgical stapling apparatus may further include at least one fluid reservoir operatively associated with at least one of the first and second clamping surfaces such that a fluid may be introduced into the fluid reservoir to deploy the first and second clamping surfaces. An outer surface of the fluid reservoir may be flexible, and also the clamping assembly may include distinct first and second fluid reservoirs operatively associated with the first and second clamping surfaces respectively, such that the first and second clamping surfaces may be deployed independently.

The first clamping surface of the clamping assembly may define a generally U-shaped perimeter. Also, at least one of the first and second clamping surfaces may include a wound treatment material.

The present disclosure also relates to a surgical apparatus for manipulating tissue. The apparatus includes a handle assembly, a tubular elongate portion extending distally from the handle assembly and including a fluid conduit extending at least partially therethrough. An end effector is coupled to a distal end of the tubular elongate portion. The end effector includes a pair of jaw members configured to move between an open configuration for receiving tissue and a closed configuration for clamping the tissue between a pair of clamping surfaces on the jaw members. Also, the end effector includes a fluid reservoir in fluid communication with the fluid conduit, wherein the fluid reservoir is inflatable to increase an effective clamping surface area of the jaw members.

The present disclosure also relates to a loading unit for use with a surgical stapling apparatus. The loading unit includes a proximal body portion configured for engagement with a portion of the surgical stapling apparatus, and an end effector disposed adjacent to a distal portion of the proximal body portion. The end effector includes an anvil assembly and a cartridge assembly wherein at least one of the cartridge assembly and the anvil assembly is movable with respect to the other between an open position wherein the cartridge assembly is substantially spaced from the anvil assembly and a closed position where the cartridge assembly and the anvil assembly are closer together. The end effector also includes an inflatable clamping assembly configured for deployment from each of the anvil assembly and the cartridge assembly, wherein the inflatable clamping assembly is in fluid communication with the proximal body portion to receive a fluid.

The proximal body portion may be configured to establish fluid communication between the loading unit and the surgical stapling apparatus upon engagement of the proximal body portion with the surgical stapling apparatus. Alternatively, the inflatable clamping assembly may be in fluid communication with a lateral opening in the proximal body portion.

BRIEF DESCRIPTION OF THE DRAWINGS

The accompanying drawings, which are incorporated in and form part of the specification, illustrate embodiments of the present disclosure when viewed with reference to the description, wherein.

DETAILED DESCRIPTION

Embodiments of the presently disclosed surgical stapling apparatus are described in detail with reference to the drawings, in which like reference numerals designate identical or corresponding elements in each of the several views. As used herein the term "distal" refers to that portion of the surgical stapler, or component thereof, farther from the user while the term "proximal" refers to that portion of the surgical stapler or component thereof, closer to the user.

Figure 1A:
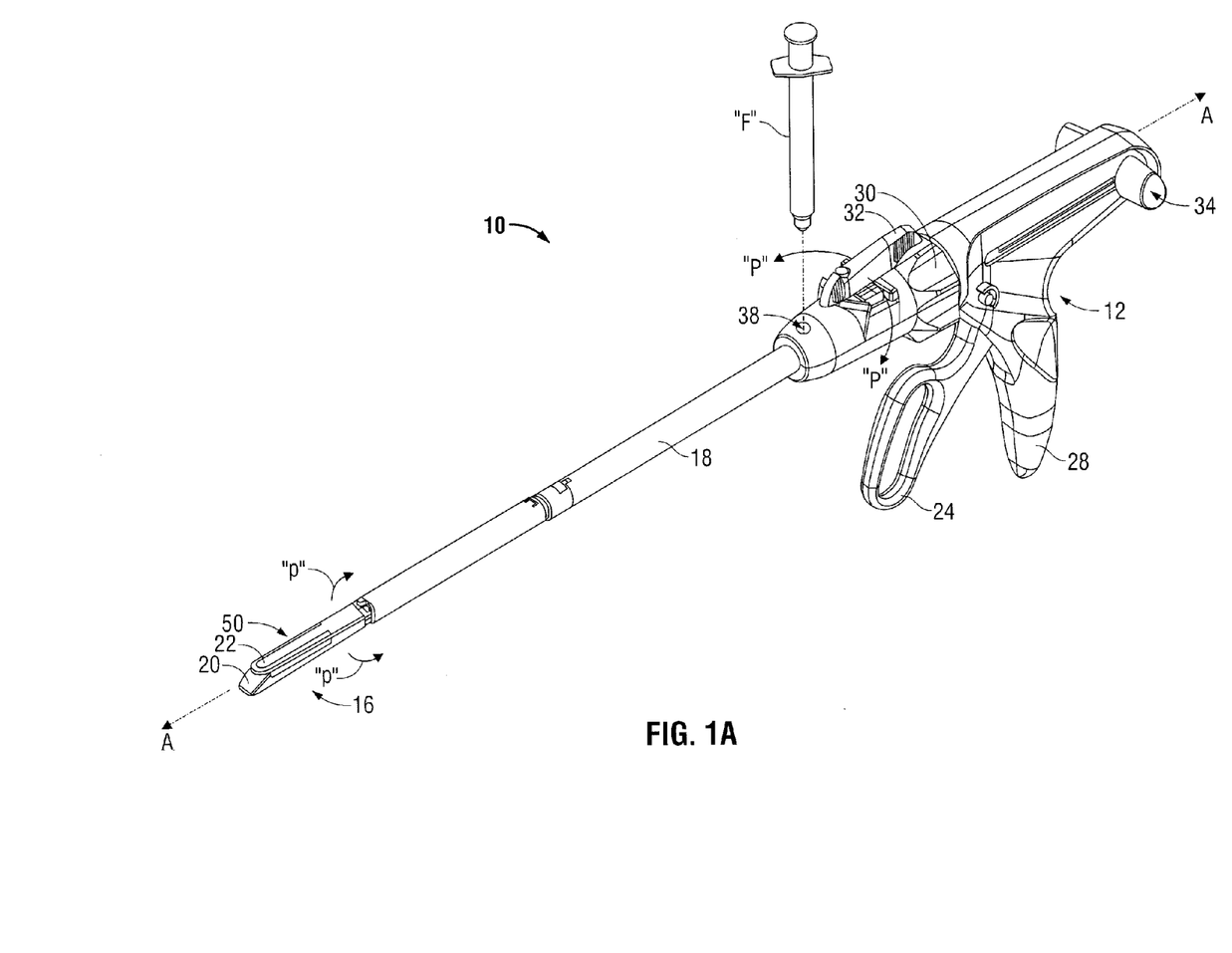
FIG. 1A is a perspective view of a surgical stapling apparatus in accordance with the present disclosure including a handle assembly and an end effector with an anvil assembly in a closed position.

Referring initially to FIG. 1A, a linear surgical stapling apparatus equipped with a clamping assembly in accordance with the present disclosure is depicted generally as reference number 10. The apparatus 10 includes a handle assembly 12 near a proximal end, an end effector 16 near a distal end and an elongate portion 18 therebetween. The end effector 16 may be positioned within a body cavity to engage tissue at a surgical site while handle assembly 12 is manipulatable by a surgeon from outside the body cavity to control the movement and operation of the end effector 16. Elongate portion 18 defines a longitudinal axis A-A. The apparatus 10 is inserted into the body cavity through a cannula (not shown) or other suitable introducer for use in endoscopic surgery.

End effector 16 includes a cartridge assembly 20, which houses a plurality of staples "s" (FIG. 1C) arranged in linear rows, and an anvil assembly 22 for forming the staples. At least one of the cartridge assembly 20 and the anvil assembly 22 is movable with respect to the other between an open position (see FIG. 2A) wherein the cartridge assembly 20 is substantially spaced from the anvil assembly 22 and a closed position (FIG. 1A) where the cartridge assembly 20 and the anvil assembly 22 are closer together. A pivotable trigger 24 of the handle assembly 12 is movable through an actuation stroke or strokes relative to a stationary grip member 28 to move cartridge assembly 20 in relation to anvil assembly 22 between the open position and the closed position and to eject the staples from cartridge assembly 20.

Figure 1B:
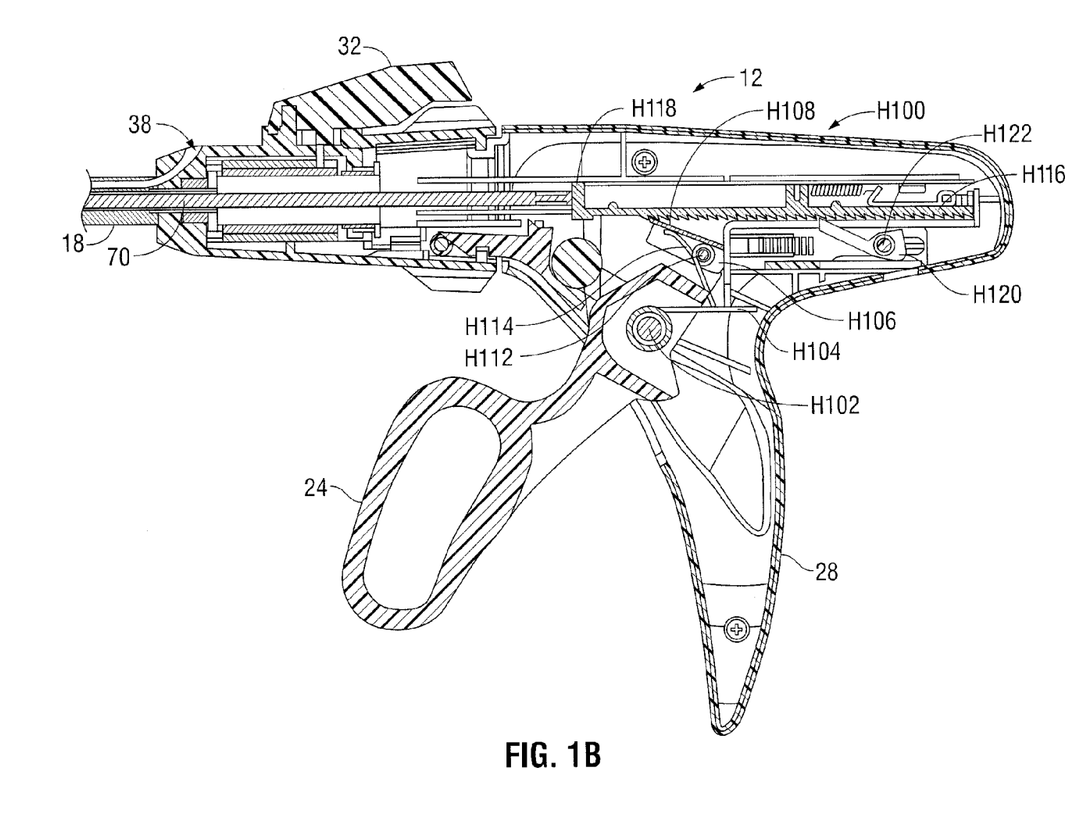
FIG. 1B is a cross sectional view of the handle assembly of FIG. 1A.

As depicted in FIG. 1B, handle assembly 12 includes a handle mechanism H100 for actuating the end effector 16. The handle mechanism H100 includes a pivot pin H102 about which trigger 24 is pivotable relative to stationary grip member 28. A biasing member such as torsion spring H104 biases the trigger 24 away from the stationary grip member 28. A driving pawl H106 having a rack engagement finger H108 is pivotally connected to the trigger 24 about a pivot pin H112. A biasing member such as torsion spring H114 urges the engagement finger H108 toward a toothed rack H116 of an actuation shaft H118. The forward end of actuation shaft H118 receives the proximal end of a control rod 70 (see FIG. 7), which extends through the elongate portion 18 toward the end effector 16.

The trigger 24 may be approximated with the stationary grip member 28 to drive the rack engagement finger H108 of the driving pawl H106 distally against the toothed rack H116. The actuation shaft H118 is thus driven linearly in a distal direction resulting in a corresponding linear distal motion of the control rod 70. A locking pawl H120 is pivotally mounted about pivot pin H122 and biased toward toothed rack H116. The locking pawl H120 tends to retain the actuation shaft H118 and the control rod 70 in a longitudinally fixed position. A more detailed description of the handle assembly of a surgical stapler and the actuation of the stapler is disclosed in commonly-owned U.S. Pat. No. 6,953,139 to Milliman et al., the entire contents of which are hereby incorporated by reference herein.

Figure 1C:
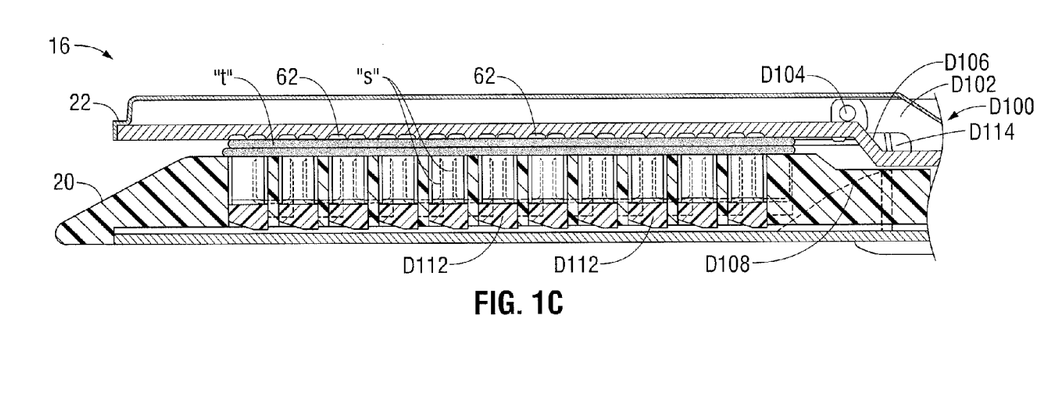
FIG. 1C is a cross sectional view of the end effector of FIG. 1A engaging tissue in a pre-firing configuration wherein staples are arranged within a cartridge assembly of the end effector.
Figure 1D:
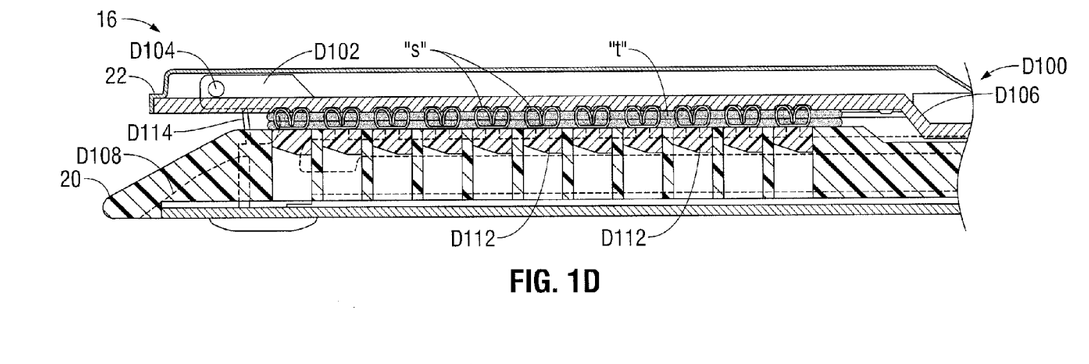
FIG. 1D is a cross sectional view of the end effector of FIG. 1C in a post-firing configuration wherein the staples are ejected from the cartridge and deformed within the tissue.

In a linear surgical stapler, for example, end effector 16 may include a drive mechanism D100 as depicted in FIGS. 1C and 1D to deploy staples "s" from the cartridge assembly 20. Drive mechanism D100 includes a drive assembly D102 attached to the control rod 70 to move with the control rod 70. Drive assembly D102 includes a cylindrical cam roller D104 for engaging a cam surface D106 on anvil assembly 22. As the cylindrical cam roller D104 engages the cam surface D106, the anvil assembly 22 is pressed against tissue "t" as the anvil assembly 22 is moved to the closed position. The drive assembly D102 abuts an actuation sled D108 such that the actuation sled D108 is driven distally through the cartridge assembly 20 by the drive assembly D102. As the actuation sled D108 translates through the cartridge assembly 20, the actuation sled D108 is moved into sequential contact with staple pushers D112. The general wedge shape of the actuation sled D108 causes the staple pushers D112 to translate vertically in the direction of the tissue "t" when contacted by the actuation sled D108 moving distally. The vertical movement of the staple pushers D112 urges staples "s" from the cartridge assembly 20, through the tissue "t" and against the staple forming pockets 62 (see also FIG. 3) formed in the anvil assembly 22. The staple forming pockets 62 are shaped to deform the staples "s" such that adjacent layers of tissue "t" are joined as depicted in FIG. 1D. The drive assembly D102 includes a knife blade D114 positioned to follow the actuation sled D108. This arrangement allows the knife blade D114 to cut the tissue "t" at a longitudinal location where the staples "s" have been applied to the tissue "t."

Figure 1E:
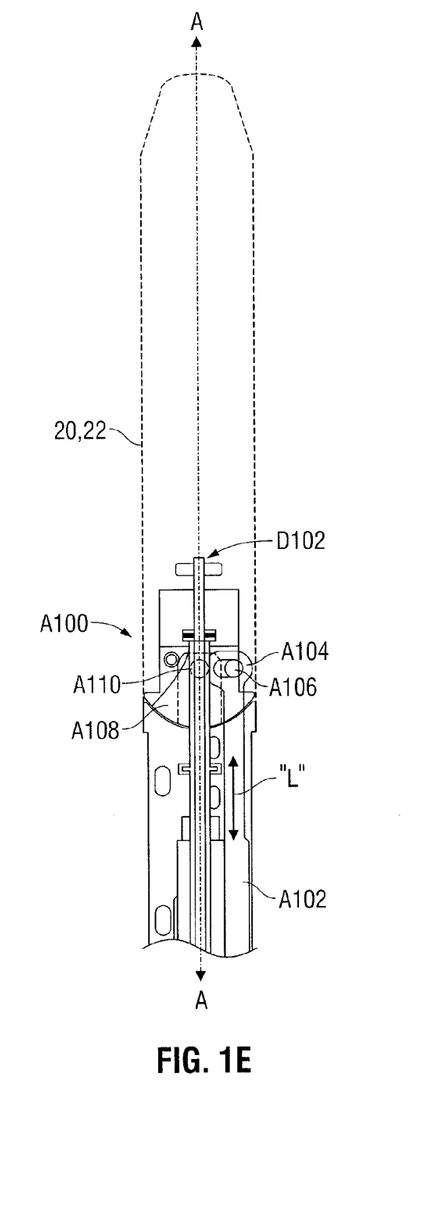
FIGS. 1E, 1F and 1G are schematic views of an articulation mechanism of the apparatus of FIG. 1 in various articulated positions.
Figure 1F:
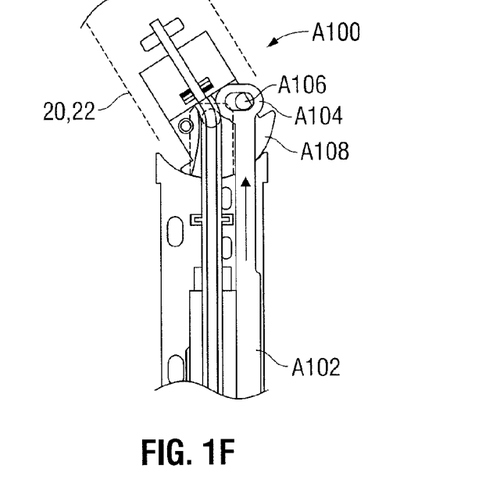
Figure 1G:
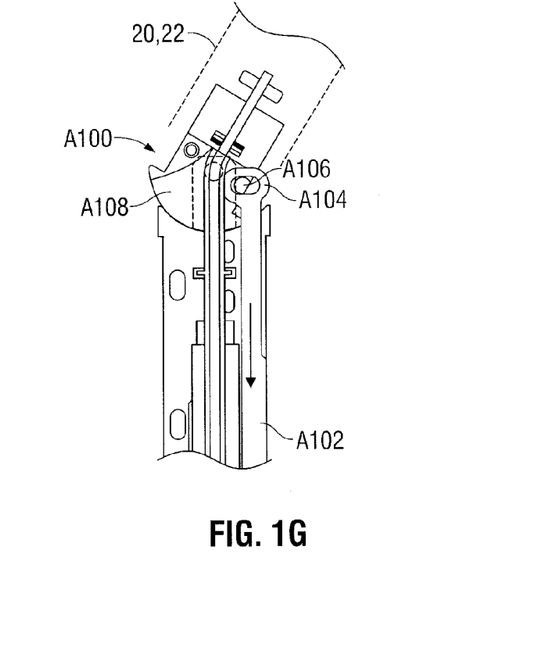

With reference to FIGS. 1A and 1E-1G, certain surgical staplers include end effectors that articulate with respect to the longitudinal axis A-A. For example, an articulation lever 32 (FIG. 1A) is pivotable in the direction of arrows "P" to cause the cartridge and anvil assemblies 20, 22 to pivot relative to the axis A-A as indicated by arrows "p." The articulation lever 32 cooperates with a cam member (not shown) to generate longitudinal motion that is transmitted through the elongate portion 18 to an articulation mechanism A100 as depicted in FIG. 1E. The articulation mechanism A100 includes an articulation link A102 configured to receive the longitudinal motion as indicated by arrows "L." The articulation link A102 is equipped with a loop A104 for engaging a projection A106 coupled to a mounting assembly A108. The mounting assembly A108 is coupled to the cartridge and anvil assemblies 20, 22 such that pivotal motion in the mounting assembly A108 is transferred to the cartridge and anvil assemblies 20, 22. The mounting assembly A108 is pivotally mounted to a pivot point A110 (depicted in phantom) having a lateral offset from projection A106. The offset causes the cartridge and anvil assemblies 20, 22 to pivot in a first direction (FIG. 1F) when the articulation link A102 is moved in a distal direction, and a second direction (FIG. 1G) when the articulation link A102 is moved in a proximal direction in response to motion of the articulation lever 32.

Handle assembly 12 is operable to control other aspects of the position, orientation and operation of the end effector 16. For example, rotation knob 30 is operable to rotate the end effector 16 about longitudinal axis A-A, and return knob 34 is operable to return the control rod 70 and drive assembly D102 to a pre-actuated position once the staples "s" have been ejected from the cartridge assembly 20.

A deployable tissue clamping structure can be incorporated into a surgical stapler as described above, or another type of surgical instrument. For example, a fluid conduit 38 extends through the elongate portion 18 between the end effector 16 and the handle assembly 12. A proximal portion of the fluid conduit 38 is depicted in FIG. 1. A fluid may be injected into the fluid conduit 38 from a fluid source "F" (a syringe, for example) to deploy the clamping assembly 50. As discussed below with reference to FIGS. 2A and 2B, the fluid may be injected under pressure such that the fluid travels distally through the fluid conduit 38 into the end effector 16. The fluid source "F" may contain air, saline or other fluids suitable for surgical applications. As depicted in FIG. 1, fluid source "F" is a distinct component from the stapling apparatus 10, but a fluid source may alternatively be incorporated into the interior of the apparatus 10 and/or associated with a control mechanism (not shown) to cause the fluid to travel distally into the end effector 16.

Figure 2A:
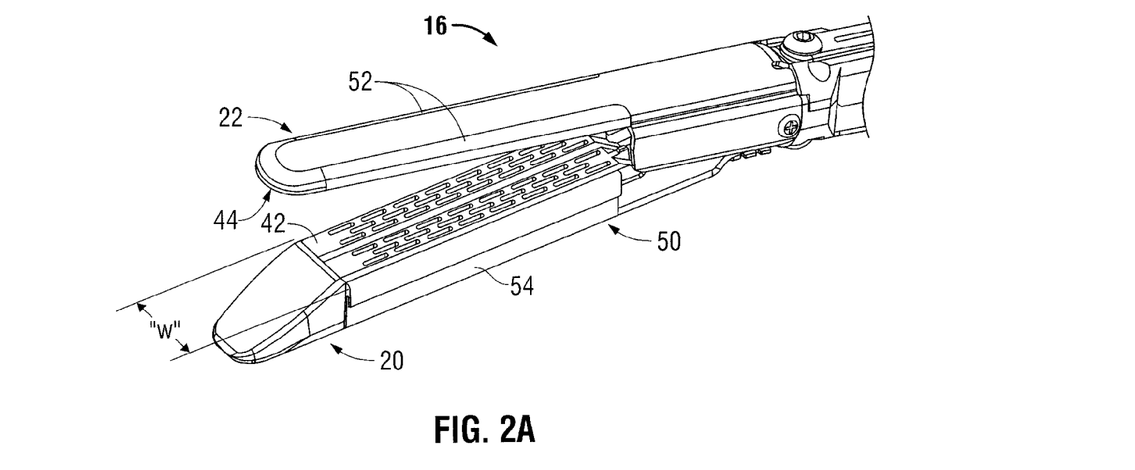
FIG. 2A is an enlarged perspective view of the end effector of FIG. 1A with the anvil assembly in an open position and depicting a clamping assembly in a undeployed configuration.

Referring now to FIG. 2A, end effector 16 is depicted with the cartridge assembly 20 and anvil assembly 22 substantially spaced from one another. In this position, tissue may be inserted between a fastener ejection surface 42 on the cartridge assembly 20 and a corresponding fastener forming surface 44 (see FIG. 3) on the anvil assembly 22. The tissue may be clamped to an appropriate thickness by approximating the cartridge assembly 20 and anvil assembly 22, and thereafter, staples may be ejected from the fastener ejection surface 42 through the tissue to be formed against the fastener forming surface 44. When a surgeon experiences difficulty clamping the tissue, or anticipates difficulty, the surgeon may deploy the clamping assembly 50.

The clamping assembly 50 includes a first pair of fluid reservoirs 52 flanking the fastener forming surface 44 and a second pair of fluid reservoirs 54 flanking the fastener ejection surface 44. As depicted in FIG. 2A, the reservoirs 52, 54 may be maintained in an undeployed condition such that a lateral width "w" of the end effector 16 may be minimized. Minimizing the lateral width "w" tends to facilitate insertion of the end effector 16 into a body cavity through a cannula, for example, and may also provide maneuverability in the body cavity to facilitate proper positioning of the end effector 16 adjacent the targeted tissue.

Figure 2B:
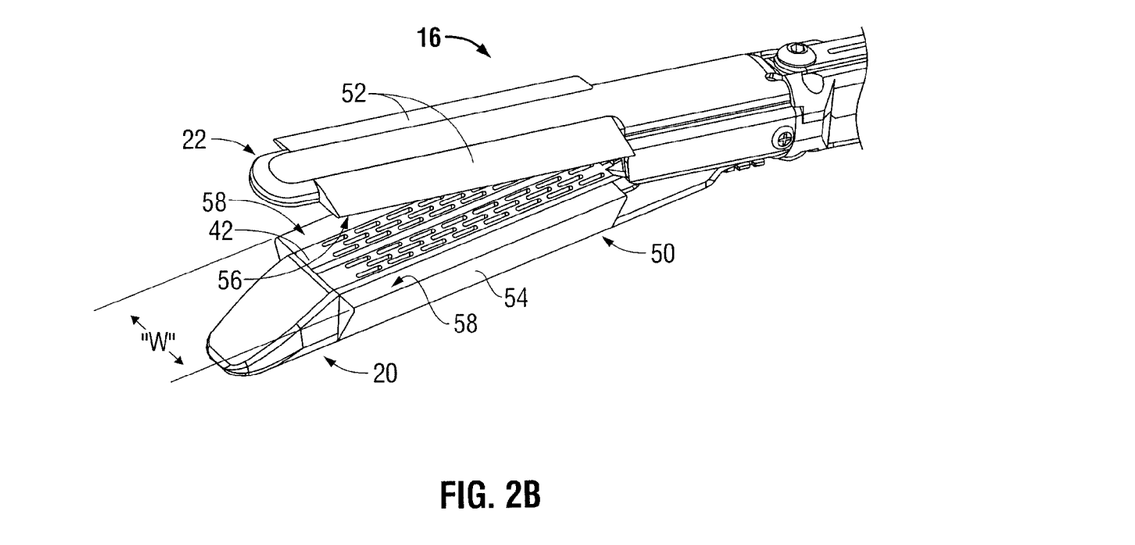
FIG. 2B is a perspective view of the end effector of FIG. 2A depicting the clamping assembly in a deployed configuration.

The clamping assembly 50 may be deployed to the configuration depicted in FIG. 2B once the targeted tissue is positioned between the cartridge and anvil assemblies 20, 22, or at any other time the surgeon deems appropriate. When deployed, the first pair of fluid reservoirs 52 define a first clamping surface 56 (see FIG. 3) extending laterally from the fastener foil iing surface 44, and the second pair of fluid reservoirs 54 define a second clamping surface 58 extending laterally from the fastener ejection surface 42. Deployment of the clamping assembly 50 defines a lateral width "W" of the end effector 16 that is greater than the lateral width "w" of the end effector 16 with the clamping assembly 50 in the undeployed configuration. The clamping surfaces 56, 58 oppose one another when the cartridge and anvil assembles 20, 22 are approximated such that the end effector 16 may maintain contact with a greater surface area of the targeted tissue than with the clamping assembly 50 in the undeployed configuration. It is envisioned that this increase of surface area that is in contact with the targeted tissue facilitates the manipulation of tissue.

Figure 2C:
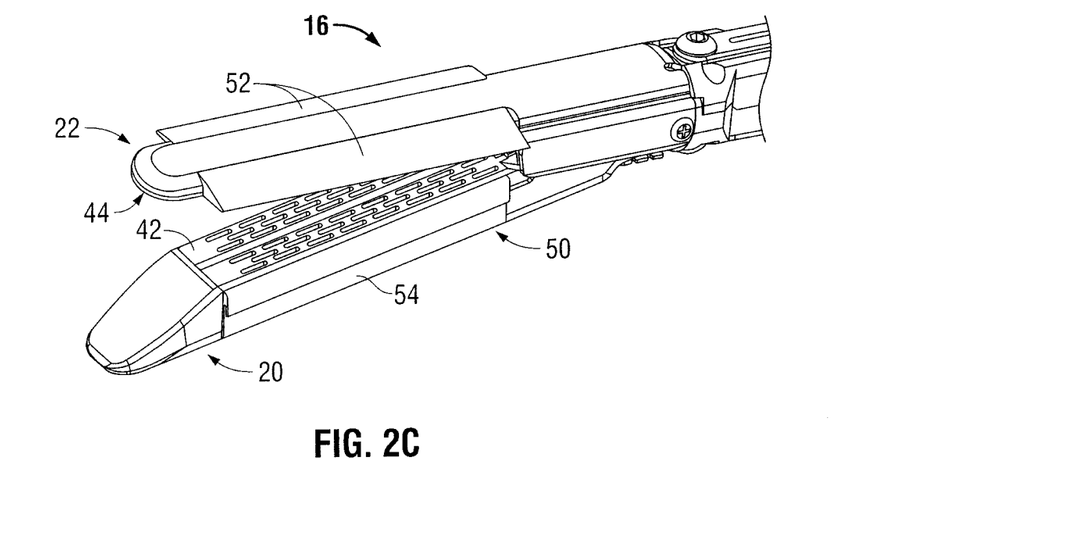
FIGS. 2C and 2D are perspective views of the end effector of FIG. 2A depicting the clamping assembly in alternate deployed configurations.
Figure 2D:
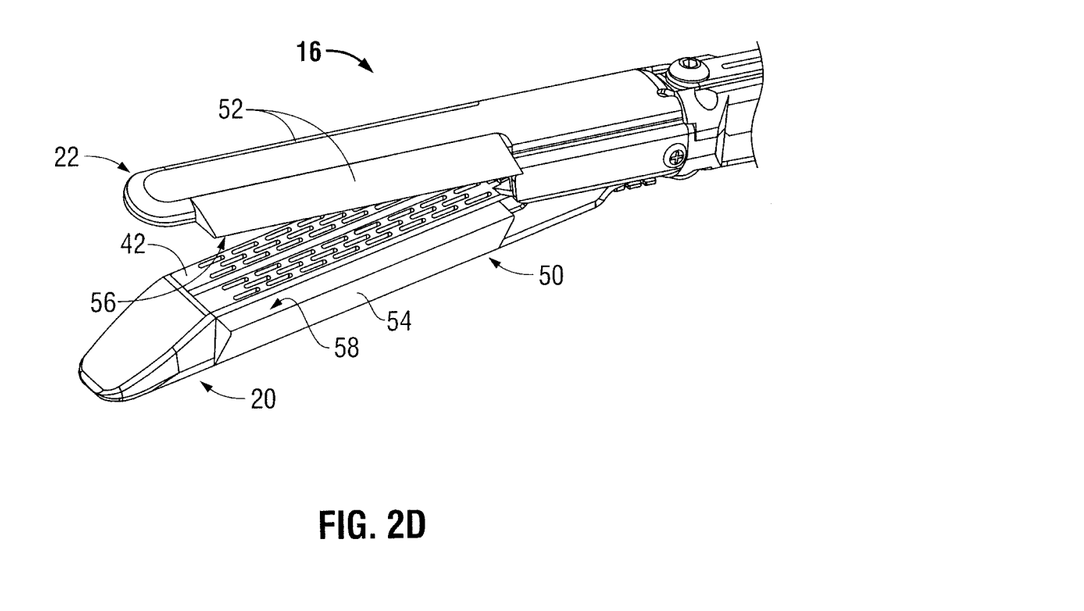

The fluid reservoirs 52, 54 may be configured for collective deployment such that each of the reservoirs 52, 54 is deployed concurrently upon a single actuation by the surgeon at the handle assembly 12. For instance, each of the reservoirs 52, 54 may fluidly communicate with the fluid conduit 38 such that injection of fluid through the fluid conduit 38 fills each of the reservoirs 52, 54 concurrently. Alternatively, the fluid reservoirs 52, 54 may be configured for individual deployment or deployment in pairs. For example, the first pair of fluid reservoirs 52 may fluidly communicate with the fluid conduit 38 while the second pair of fluid reservoirs 54 fluidly communicates with an additional fluid conduit (not shown). This configuration offers an additional degree of control to a surgeon. For example, a surgeon may deploy reservoirs 52 while maintaining reservoirs 54 in an undeployed configuration as depicted in FIG. 2C. It is also envisioned that the reservoirs 52, 54 may be configured to permit deployment of the reservoirs 52, 54 on one lateral side of the end effector 16 while maintaining the reservoirs 52, 54 on another lateral side of the end effector 16 in an undeployed configuration as depicted in FIG. 2D. The reservoirs 52, 54 can be deployed as desired to spread the clamping force applied to the tissue and/or accommodate tissue having areas of different thicknesses.

Figure 3:
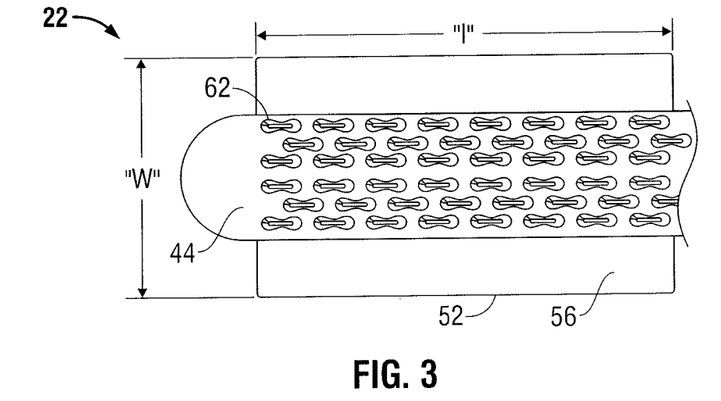
FIG. 3 is a plan view of a clamping surface of the anvil assembly of FIG. 2B.

Referring now to FIG. 3, the fastener forming surface 44 of the anvil assembly 22 includes rows of staple forming pockets 62 arranged in rows to oppose the staples housed within the cartridge assembly 20 (FIG. 1). The first pair of fluid reservoirs 52 extends laterally on opposing sides of the fastener forming surface 44 to define the first pair of clamping surfaces 56. The clamping surfaces 56 extend in a lateral direction to define the lateral width "W" as described above, and extend in a longitudinal direction so as to have a sufficient length "l" to flank an entire row of staple forming pockets 62, for example. Thus, lateral support may be provided to tissue adjacent each one of the staple forming pockets 62.

Figure 4:
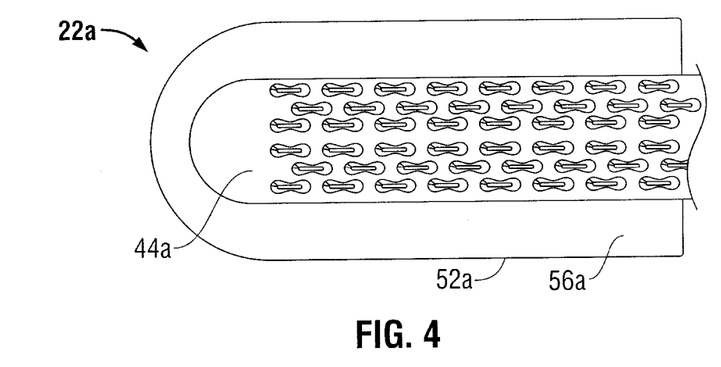
FIG. 4 is a plan view of an alternate embodiment of a clamping surface of an anvil assembly in accordance with the present disclosure.

FIG. 4 depicts an alternate embodiment of an anvil assembly 22a. A fluid reservoir 52a extends along two longitudinal sides of the anvil assembly 22a to flank the fastener forming surface 44a, and also along a transverse side adjacent the distal end of the fastener forming surface 44a. A clamping surface 56a thus defines a generally U-shaped perimeter around the fastener forming surface 44a. A similar clamping surface (not shown) could be arranged around a corresponding fastener ejection surface to oppose the clamping surface 56a.

Figure 5:
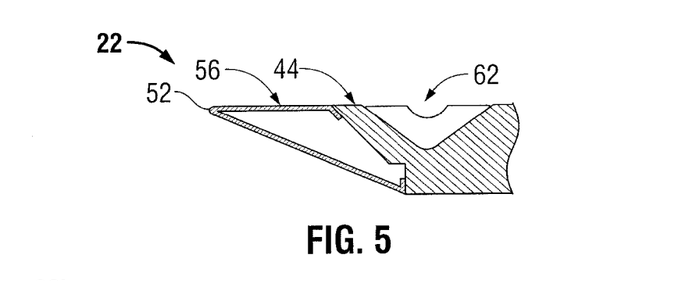
FIG. 5 is a partial transverse cross-sectional view of the anvil assembly of FIG. 3.

Referring now to FIG. 5, clamping surface 56 is configured to lie flush with the fastener forming surface 44. Exterior walls of the fluid reservoir 52 may be constructed of a rigid or semi-rigid material to maintain a generally flat external geometry when inflated or otherwise filled with a fluid. The pressure of the fluid within the reservoir 52 may be varied to exhibit a similar or dissimilar rigidity with respect to the fastener forming surface 44 at the discretion of the surgeon.

Figure 6:
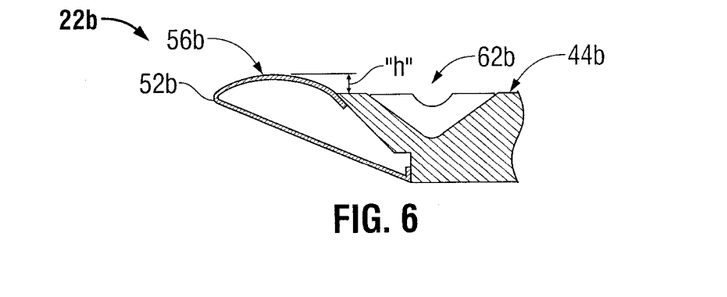
FIG. 6 is a partial transverse cross-sectional view of an alternate embodiment of an anvil assembly in accordance with the present disclosure.

FIG. 6 depicts an alternate embodiment of an anvil assembly 22b. A clamping surface 56b is configured to extend to a height "h" above a fastener forming surface 44b. Exterior walls of reservoir 52b may be constructed of a flexible material such that the height "h" may be varied according to the amount or pressure of the fluid applied to the reservoir 52b. Clamping tissue against the clamping surface 56b may tend to deform the reservoir 52b, and may be less traumatic to the tissue as compared with a rigid clamping surface.

The clamping surfaces 56, 58, 56a and 56b may be retracted by evacuating and deflating the reservoirs 52, 54, 52a and 52b. Fluid may be actively withdrawn by generating a reduced pressure at the fluid source "F" (FIG. 1). In this manner, the fluid may be returned to the fluid source "F" under the influence of a suction force. Alternatively, the reservoirs 56, 58, 56a and 56b may be evacuated by establishing a fluid flow path between the reservoirs 56, 58, 56a and 56b and the atmosphere, thus permitting the fluid to vent. Retracting the clamping surfaces 56, 58, 56a and 56b would facilitate removal of the apparatus 10 through a cannula, for example.

Any of the clamping surfaces 56, 58, 56a and 56b of the present disclosure may be constructed to include a wound treatment material. The material forming exterior walls of the fluid reservoirs 52, 54, 52a and 52b may be impregnated with the wound treatment material, or the clamping surfaces 56, 58, 56a and 56b may be coated with the wound treatment material. Alternatively or additionally, the wound treatment material can be contained in the reservoir or reservoirs 52, 54, 52a and 52b, and deployed therefrom. The reservoir walls can be puncturable or include perforations that allow leakage of the wound treatment material to apply the material to tissue. The wound treatment material may include an adhesive sealant, a hemostat such as a fibrin based material or a medicament such as a drug, enzyme, growth factor or a diagnostic agent. Many other possible wound treatment materials are described in U.S. Pat. No. 7,455,682, which is incorporated by reference herein in its entirety.

Figure 7:
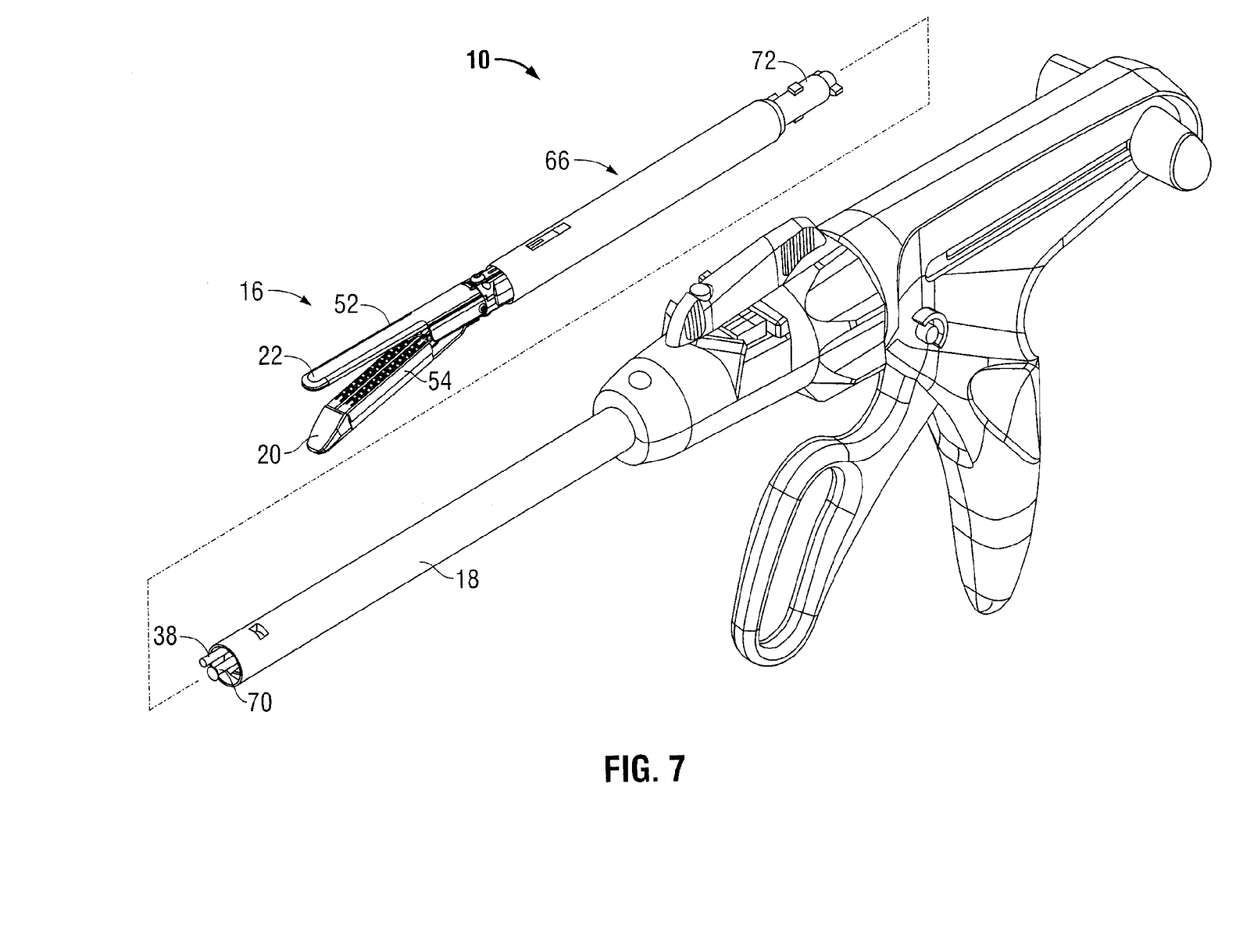
FIG. 7 is an exploded perspective view of the surgical stapling apparatus of FIG. 1 depicting a loading unit separated from an elongate portion of the surgical stapling apparatus.

Referring now to FIG. 7, surgical stapling apparatus 10 is depicted with a loading unit 66 separated from elongate portion 18. The loading unit 66 includes the end effector 16 and may be configured as a single use loading unit (SULU) or a disposable loading unit (DLU) as described in U.S. Pat. No. 7,143,924, which is incorporated by reference herein. The loading unit 66 is releasable from the elongate portion 18 such that loading unit 66 may be removed and replaced after using the surgical stapling apparatus 10. In so doing, the drive assembly of the apparatus 10 is replaced, and a fresh knife is supplied, whenever the apparatus is re-loaded. Alternatively, the surgical stapling apparatus may include a replaceable stapling cartridge which is re-loaded into the jaws of the apparatus.

The control rod 70 extends through the elongate portion 18. The jaw members are defined by the cartridge assembly 20 and the anvil assembly 22. Also, fluid conduit 38 extends through the elongate portion 18 such that the reservoirs 52 and 54 may be deployed to increase an effective clamping surface area and apply pressure to tissue adjacent the jaw members as described above.

Loading unit 66 includes a proximal body portion 72 configured for engagement with the elongate portion 18. Engagement of the elongate portion 18 and the proximal body portion establishes an operable connection between the control rod 70 and the drive assembly that interacts with the cartridge assembly 20 and anvil assembly 22. Connection of the loading unit also establishes fluid communication between the fluid conduit 38 and the reservoirs 52 and 54.

Figure 8:
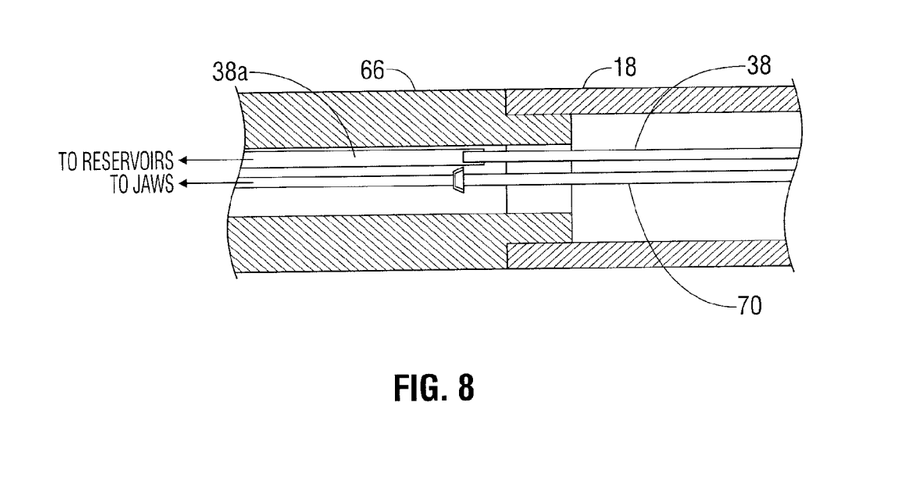
FIG. 8 is a schematic view of the loading unit and elongate portion of FIG. 7 in an engaged configuration.

Referring now to FIG. 8, the loading unit 66 includes a fluid conduit portion 38a. When the loading unit 66 is connected with the elongate portion 18 of the apparatus 10, a substantially fluid-tight connection is established between the fluid conduit portion 38a and the fluid conduit 38 by a quick-disconnect or other mechanism. The fluid conduit portion 38a extends distally to fluidly communicate with reservoirs 52, 54. The loading unit 66 may engage the elongate portion 18 with a bayonet, quarter-turn, or similar mechanism requiring both longitudinal and rotational movement between the two components 66, 18. Thus, the fluid conduit portion 38a, fluid conduit 38 or the connection established therebetween may be sufficiently flexible to accommodate the relative motion associated with the connection of loading unit 66 and the elongate portion 18.

Figure 9:
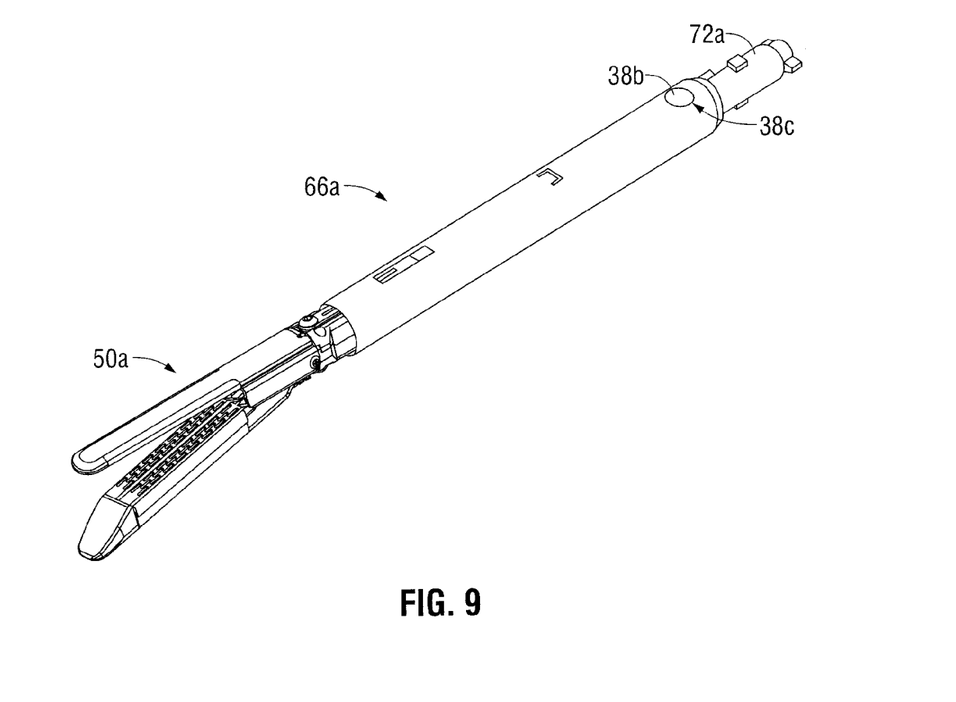
FIG. 9 is a perspective view of an alternate embodiment of a loading unit in accordance with the present disclosure.

Referring now to FIG. 9, a loading unit 66a is configured for use with a surgical stapling apparatus (not shown) that does not necessarily include a fluid conduit extending through an elongate portion. Loading unit 66a includes a fluid conduit portion 38b extending between an opening 38c in a proximal body portion 72a of the loading unit 66a and a clamping assembly 50a. The proximal body portion 72a is long enough and the opening 38c is positioned sufficiently proximally such that when the loading unit 66a is inserted into a cannula, the lateral opening 38c is exposed (i.e., located proximally of the cannula) to permit introduction of a fluid from a fluid source "F" (FIG. 1). A syringe, for example, may be provided as fluid source "F." A syringe permits fluid to be introduced under pressure through the lateral opening 38c, through fluid conduit portion 38b, and into clamping assembly 50a to deploy the clamping assembly 50a. Once the clamping assembly 50a has been deployed, the syringe permits evacuation of the fluid from clamping assembly 50a. The clamping assembly 50a may thus be deployed and retracted even when the loading unit 66a is coupled to a surgical stapling apparatus devoid of a fluid conduit extending through an elongate portion.

Many components of surgical stapling apparatus 10 are substantially as described in U.S. Pat. No. 6,669,073, which is incorporated herein in its entirety by reference. It is contemplated that the presently disclosed clamping assembly may be used in association with other known stapling devices of both endoscopic and open construction. These devices include articulating and non-articulating devices as well as reusable and non-reusable devices. Examples of such devices are disclosed in U.S. Pat. Nos. 6,202,914 and 6,250,532, which are also incorporated herein in their entirety by reference.

Figure 10:
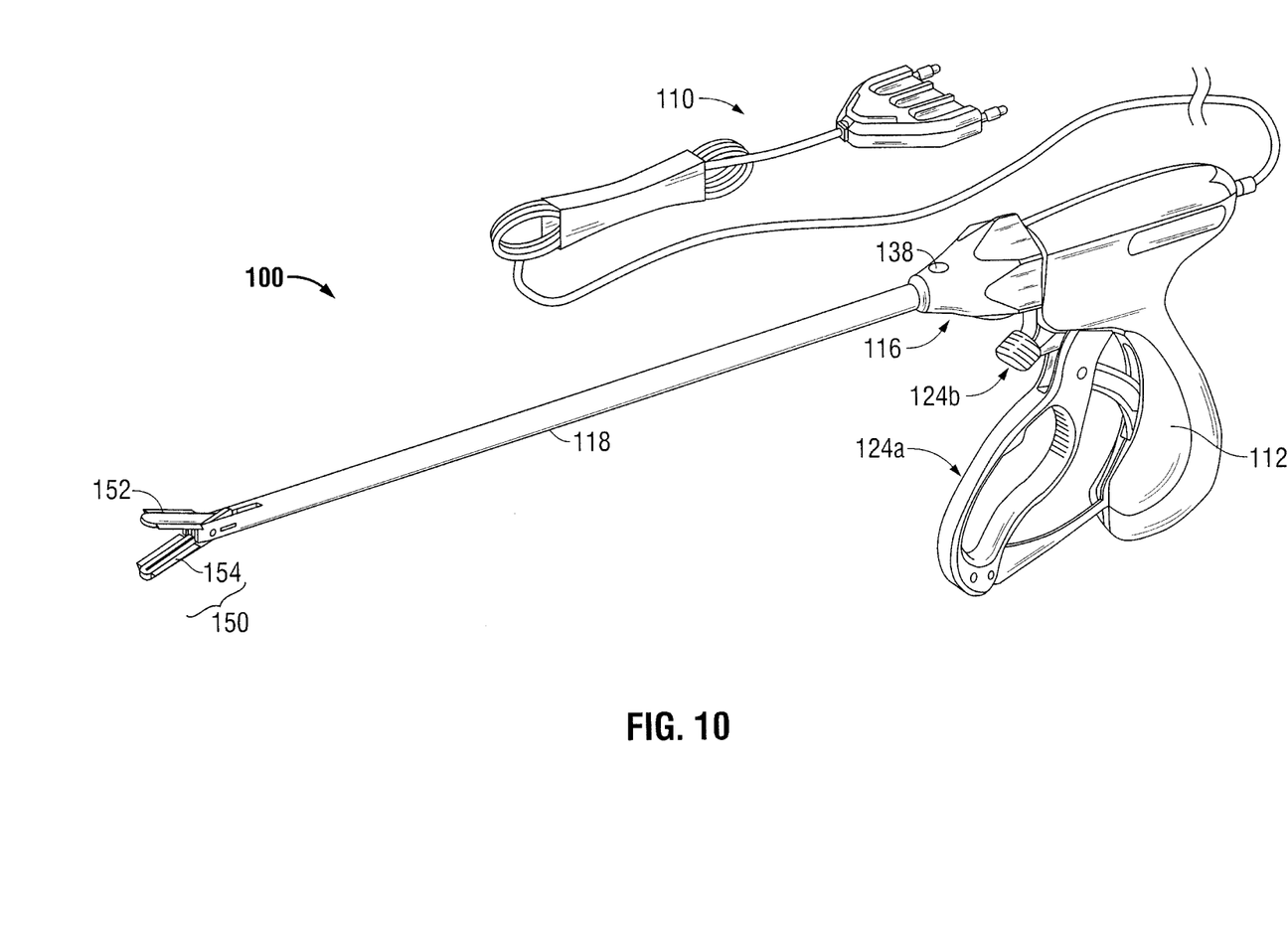
FIG. 10 is a perspective view of an electrosurgical apparatus in accordance with the present disclosure.

Referring now to FIG. 10, an electrosurgical apparatus 100 may also embody various aspects of the present disclosure. Electrosurgical apparatus 100 includes a connector assembly 110 for connection to a source of electrosurgical energy (not shown). The use of an electrosurgical apparatus to apply electrosurgical energy to tissue is generally described in U.S. Pat. No. 7,083,618, which is incorporated herein in its entirety by reference.

Electrosurgical apparatus 100 includes a handle assembly 112 near a proximal end, an end effector 116 near a distal end and an elongate portion 118 therebetween. The end effector 116 may be positioned within a body cavity to engage tissue at a surgical site while handle assembly 112 is manipulatable by a surgeon from outside the body cavity to control the movement and operation of the end effector 116. Handle assembly 112 includes a movable handle 124a, which may be manipulated to open and close the end effector 116, and a trigger 124b, which may be manipulated to initiate an electrosurgical current.

A fluid conduit 138 extends from the handle assembly 112, through elongate portion 118 to a clamping assembly 150 at the end effector 116. Thus, a fluid may be injected into the fluid conduit 138 from a fluid source "F" (FIG. 1) from outside the body to deploy the clamping assembly 150 within a body cavity. The clamping assembly 150 includes a pair of reservoirs 152, 154 in fluid communication with the fluid conduit 138. The reservoirs 152, 154 may be filled with the fluid to extend laterally from tissue engaging surfaces of the end effector 116 as depicted in FIG. 10. This increases an effective clamping surface area of the end effector 116. The clamping assembly 150 may be undeployed by evacuating the reservoirs 152, 154 for insertion and withdrawal of the end effector 116 through a cannula, for example.

It will be understood that various modifications may be made to the embodiments disclosed herein. For example, a clamping assembly may include hinged plates configured for selective lateral deployment or other non-inflatable mechanisms may be employed. Moreover, the size, angles and/or curves of the various components described above may be modified to better suit a particular surgical procedure. Therefore, the above description should not be construed as limiting, but merely as exemplifications of various embodiments. Those skilled in the art will envision other modifications within the scope and spirit of the claims appended hereto.

What is claimed is:

1. A method of grasping tissue, the method comprising:
providing a surgical apparatus including:
a handle assembly;
a tubular elongate portion extending distally from the handle assembly and including a fluid conduit extending at least partially therethrough; and
an end effector disposed adjacent a distal end of the tubular elongate portion, the end effector including:
a first jaw member including a first opposed surface;
a second jaw member including a second opposed surface; and
a fluid reservoir in fluid communication with the fluid conduit;
inserting the end effector through a surgical access device;
positioning the end effector adjacent tissue after inserting the end effector through the surgical access device;
inflating the fluid reservoir to increase an effective clamping surface area over which the first and second jaw members oppose one another; and
moving the second jaw member relative to the first jaw member between an open position and an approximated position.

2. The method of claim 1, wherein the first jaw member includes an anvil assembly including a fastener forming surface thereon, wherein the second jaw member includes a cartridge assembly including a fastener ejection surface thereon, and wherein the method further comprises stapling tissue with the surgical apparatus.

3. The method of claim 1, wherein inflating the fluid reservoir to increase an effective clamping surface area over which the first and second jaw members oppose one another includes increasing a clamping surface area of at least one of the first opposed surface and the second opposed surface.

4. The method of claim 1, wherein inflating the fluid reservoir to increase an effective clamping surface area over which the first and second jaw members oppose one another includes increasing a clamping surface area of the first opposed surface and increasing a clamping surface area of the second opposed surface.

5. The method of claim 1, wherein inflating the fluid reservoir to increase an effective clamping surface area over which the first and second jaw members oppose one another includes deploying the fluid reservoir to extend laterally from at least one of the first jaw member and the second jaw member.

6. The method of claim 1, wherein inflating the fluid reservoir to increase an effective clamping surface area over which the first and second jaw members oppose one another includes deploying the fluid reservoir to extend laterally from two lateral sides of both the first jaw member and the second jaw member.

7. The method of claim 1, wherein the surgical apparatus includes a connector assembly for connection to a source of electrosurgical energy, and wherein the method further comprises connecting the surgical apparatus to the source of electrosurgical energy.

8. The method of claim 1, wherein the first jaw member includes an anvil assembly including a fastener forming surface thereon, wherein the second jaw member includes a cartridge assembly including a fastener ejection surface thereon, and wherein the method further comprises stapling tissue with the surgical apparatus, followed by deflating the fluid reservoir to decrease the effective clamping surface area over which the first and second jaw members oppose one another.

9. The method of claim 8, further including removing the surgical apparatus through the surgical access device after the fluid reservoir has been deflated.

10. The method of claim 1, wherein inflating the fluid reservoir to increase an effective clamping surface area over which the first and second jaw members oppose one another includes delivering a fluid through the fluid conduit and at least partially into the fluid reservoir.

11. A method of grasping tissue, the method comprising:
provinding a surgical apparatus including:
  a handle assembly;
  an elongate portion extending distally from the handle assembly; and
  an end effector disposed adjacent a distal end of the elongate portion, the end effector including:
    a first jaw member;
    a second jaw member;
    a fluid reservoir disposed in mechanical cooperation with at least one of the first jaw member or the second jaw member; and
    a fluid conduit disposed in fluid communication with the fluid reservoir;
inserting the end effector through a surgical access device;
positioning the end effector adjacent tissue after inserting the end effector through the surgical access device;
delivering fluid through the fluid conduct and into the fluid reservoir; and
moving the second jaw member relative to the first jaw member between an open position and an approximated position.

12. The method of claim 11, wherein the first jaw member includes an anvil assembly including a fastener forming surface thereon, wherein the second jaw member includes a cartridge assembly including a fastener ejection surface thereon, and wherein the method further comprises stapling tissue with the surgical apparatus.

13. The method of claim 11, wherein the surgical apparatus includes a connector assembly for connection to a source of electrosurgical energy, and wherein the method further comprises connecting the surgical apparatus to the source of electrosurgical energy.

14. The method of claim 11, wherein the first jaw member includes an anvil assembly including a fastener forming surface thereon, wherein the second jaw member includes a cartridge assembly including a fastener ejection surface thereon, and wherein the method further comprises stapling tissue with the surgical apparatus, followed by removing fluid from the fluid reservoir.

15. The method of claim 14, further including removing the surgical apparatus through the surgical access device after removing fluid from the fluid reservoir.

* * * * *